US008478791B2

(12) United States Patent
Ganesh et al.

(10) Patent No.: US 8,478,791 B2
(45) Date of Patent: Jul. 2, 2013

(54) INTEROPERABILITY ACROSS HETEROGENEOUS TAXONOMIES

(75) Inventors: Jai Ganesh, Bangalore (IN); Seema Pandey, Pune (IN); Niranjan Varadarajan Iyengar, Mumbai (IN); Pallavi Mokkarala, Cypress, TX (US)

(73) Assignee: Infosys Limited, Bangalore (IN)

( * ) Notice: Subject to any disclaimer, the term of this patent is extended or adjusted under 35 U.S.C. 154(b) by 891 days.

(21) Appl. No.: 11/854,498

(22) Filed: Sep. 12, 2007

(65) Prior Publication Data

US 2008/0109254 A1    May 8, 2008

(30) Foreign Application Priority Data

Sep. 12, 2006    (IN) ............................ 1654/CHE/2006

(51) Int. Cl.
*G06F 7/00*    (2006.01)
*G06F 17/30*    (2006.01)

(52) U.S. Cl.
USPC ............................ 707/803; 707/804; 707/805

(58) Field of Classification Search
USPC ........................................ 707/803, 804, 805
See application file for complete search history.

(56) References Cited

U.S. PATENT DOCUMENTS

| | | | |
|---|---|---|---|
| 6,438,533 B1 | 8/2002 | Spackman et al. | |
| 6,675,161 B1 * | 1/2004 | Suchter | 707/5 |
| 6,711,585 B1 * | 3/2004 | Copperman et al. | 707/104 |
| 6,980,984 B1 | 12/2005 | Huffman et al. | |
| 7,225,411 B1 * | 5/2007 | Stoner et al. | 715/760 |
| 7,392,255 B1 * | 6/2008 | Sholtis et al. | 707/203 |
| 7,668,737 B2 * | 2/2010 | Streepy, Jr. | 705/3 |
| 2003/0167283 A1 | 9/2003 | Remsen et al. | |
| 2004/0088325 A1 * | 5/2004 | Elder et al. | 707/104.1 |
| 2004/0230572 A1 * | 11/2004 | Omoigui | 707/3 |
| 2005/0071362 A1 | 3/2005 | Nelson et al. | |
| 2006/0020444 A1 | 1/2006 | Cousineau et al. | |
| 2006/0074519 A1 * | 4/2006 | Barker et al. | 700/213 |
| 2007/0226246 A1 * | 9/2007 | Dheap et al. | 707/102 |

FOREIGN PATENT DOCUMENTS

| | | |
|---|---|---|
| EP | 1345130 | 9/2003 |
| WO | WO 2005/069932 | 8/2005 |

OTHER PUBLICATIONS

Juliana Brixey, Tood R Johnson, Jiajie Zhang, Evaluating a Medical Error Taxonomy, Proceeding of AMIA2002 (2002).*
Burgun, Anita et al., Mapping the UMLS Semantic Network into General Ontologies, Proc. AMIA Symp (2001), pp. 81-85.*
Chang et al., "The JCAHO patient safety event taxonomy: a standardized terminology and classification schema for near misses and adverse events," *International Journal for Quality in Health Care*, 17(2): 95-105 (2005).
"Patient Safety Solution: A part of Infosys' Clinical Transformation HER/PHR Solution Suite," Infosys Technologies Limited, 2 pages (2006).

(Continued)

*Primary Examiner* — Mariela Reyes
(74) *Attorney, Agent, or Firm* — Klarquist Sparkman, LLP

(57) ABSTRACT

Interoperability across two or more heterogeneous clinical medical error taxonomies can be improved by associating categories in various taxonomies with one or more categories in a master taxonomy. These associations can be expressed using a unique identifier, e.g., a number that identifies one or more categories in the master taxonomy. Various aspects of the associations and/or one or more master taxonomies can be modified by users of a system employing embodiments of the technologies described herein. Searches of clinical medical error records can also be aided using the technologies described herein.

18 Claims, 13 Drawing Sheets

OTHER PUBLICATIONS

"Medical Ontology Research," The Lister Hill National Center for Biomedical Communications, http://lhncbc.nlm.nih.gov/lhc/servlet/Turvine/template/research,langproc,MedicalOntology.vm, 1 page, last updated Jul. 9, 2007.

Turley et al, "Comprehensive Medical Error Ontology for the Codification of Published Literature," *Cognitive Studies*, 13:(1):6-16 (Mar. 2006).

* cited by examiner

Fig. 5

| D1 | D2 | D3 | D4 | D5 | D6 | D7 | D8 | D9 | D10 | D11 | D12 | D13 | D14 | D15 | D16 | D17 | D18 |
|----|----|----|----|----|----|----|----|----|-----|-----|-----|-----|-----|-----|-----|-----|-----|
| 1  | 0  | 0  | 0  | 0  | 2  | 0  | 0  | 6  | 0   | 0   | 1   | 0   | 0   | 0   | 0   | 0   | 0   |

INTEROPERABILITY ACROSS HETEROGENEOUS TAXONOMIES

CROSS-REFERENCE TO RELATED APPLICATION

This application claims the benefit of Indian Patent Application No. 1654/CHE/2006, titled "SYSTEM AND METHOD FOR IMPROVING INTEROPERABILITY ACROSS HETEROGENEOUS TAXONOMIES," filed Sep. 12, 2006, which is incorporated herein by reference.

FIELD

The disclosed technologies relate generally to interoperating among two or more heterogeneous clinical medical error taxonomies.

BACKGROUND

Clinical medical errors (also called "clinical errors") generally describe human and/or organizational errors in the field of medicine. These errors sometimes have harmful effects on patients. It is often helpful to categorize these errors in a database to better understand their causes and to develop appropriate solutions.

Medical professionals within different fields, geographic locations and/or organizations currently use different taxonomies to record and categorize clinical medical errors. Uncoordinated taxonomic structures can make it difficult to compare and study errors recording using heterogeneous taxonomies.

SUMMARY

Interoperability across two or more heterogeneous clinical medical error taxonomies can be improved by associating categories in various taxonomies with one or more categories in a master taxonomy. These associations can be expressed using a unique identifier, e.g., a number that identifies one or more categories in the master taxonomy. Various aspects of the associations and/or one or more master taxonomies can be modified by users of a system employing embodiments of the technologies described herein. Searches of clinical medical error records can also be aided using the technologies described herein.

In some embodiments, a system comprises: a first software component configured to receive a user-provided description for a clinical medical error category; a second software component configured to associate a unique identifier with the user-provided description; and a third software component comprising a mapping of a plurality of unique identifiers to a plurality of corresponding portions of two or more taxonomies for classifying clinical medical errors. In particular embodiments the unique identifier associated with the user-provided description comprises a plurality of level-specific indicators, and in further embodiments the plurality of level-specific indicators comprise respective numerical values. In additional embodiments the system further comprises a set of one or more rules for managing data in the second and third software components. In further embodiments, at least one of the first software component, the second software component and the third software component is configured to be executed on a first computer, and at least one of the first software component, the second software component and the third software component is configured to be executed on a second computer. Some embodiments further comprise a search software component configured to search clinical medical error data based on the mapping of the plurality of unique identifiers. Additional embodiments further comprise an administrative software component configured to modify one or more aspects of at least one of the first software component, the second software component and the third software component. In some cases the administrative software component is configured to approve one or more modifications to the mapping of the plurality of unique identifiers to the plurality of corresponding portions of the two or more taxonomies for classifying clinical medical errors. In particular embodiments the mapping of the plurality of unique identifiers to the plurality of corresponding portions of two or more taxonomies identifies one or more clinical medical error types common to the two or more taxonomies.

In further embodiments, one or more computer-readable media comprise a data structure for classifying a clinical medical error, the data structure comprising: an indicator of a first category in a first clinical medical error taxonomy; and an indicator of a category in a second clinical medical error taxonomy that is associated with the first category in the first clinical medical error taxonomy. Some embodiments further comprise an indicator of a second category in the first clinical medical error taxonomy. In additional embodiments the indicator of the first category is a first number and the indicator of the second category is a second number. In particular embodiments the format of the second indicator varies as a function of the first indicator.

In still further embodiments, one or more computer-readable media comprise instructions that cause a computer to perform a method comprising: receiving a description of a first clinical medical error category in a first clinical medical error taxonomy; creating a first association of the description of the first clinical medical error category in the first clinical medical error taxonomy with a unique identifier of a second clinical medical category in a second clinical medical error taxonomy; and storing an indication of the association in one or more computer-readable media. In some cases the description of the first clinical medical error category in the first clinical medical error taxonomy is received over a network. In particular embodiments the method further comprises receiving update information from a user for modifying the second clinical medical error taxonomy. Sometimes the update information is provided after being approved by an administrator. In additional embodiments the update information is provided by a plurality of users. In some embodiments, the method further comprises: receiving a description of a third clinical medical error category in a third clinical medical error taxonomy; creating an association of the description of the third clinical medical error category in the third clinical medical error taxonomy with the unique identifier of the second clinical medical category in the second clinical medical error taxonomy; and storing an indication of the association of the description of the third clinical medical error category in the third clinical medical error taxonomy with the unique identifier in one or more computer-readable media. In select embodiments the method further comprising: making a determination, based at least in part on the unique identifier, whether a clinical medical error associated with the first clinical medical error category in the first clinical medical error taxonomy is considered to be similar to a clinical medical error associated with the third clinical medical error category in a third clinical medical error taxonomy; and storing the determination in one or more computer-readable media.

The foregoing and other features and advantages of the disclosed technologies will become more apparent from the following detailed description, which proceeds with reference to the accompanying figures.

BRIEF DESCRIPTION OF THE DRAWINGS

FIG. 5 shows a table depicting an exemplary embodiment of one format for a unique identifier.

DETAILED DESCRIPTION

Figure 1:
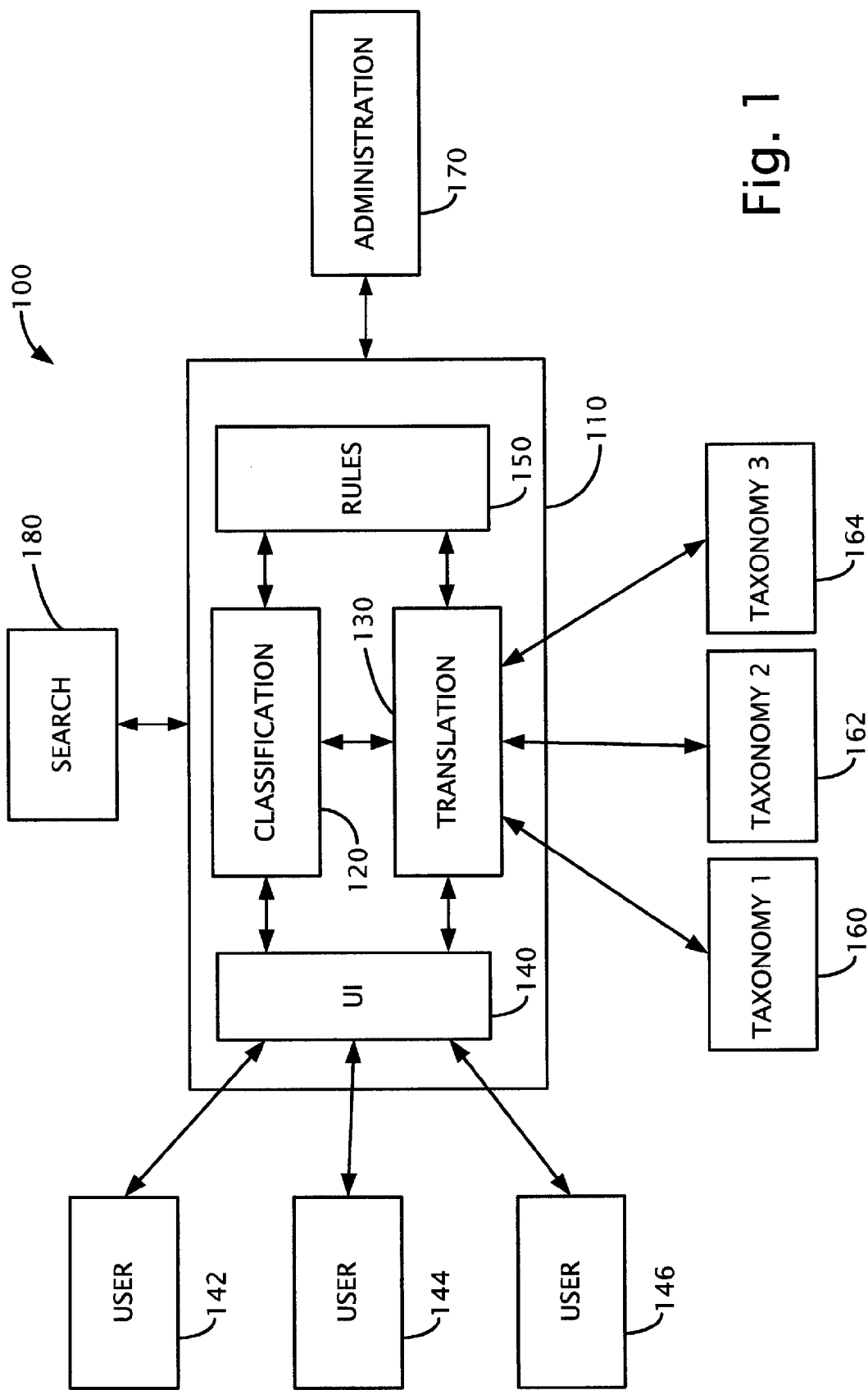
FIG. 1 shows a block diagram of an exemplary embodiment of a system that can be used for managing clinical medical error information, particularly clinical medical error information that is described using two or more heterogeneous taxonomies.

Disclosed below are representative embodiments of heterogeneous taxonomy interoperation techniques and associated apparatus that should not be construed as limiting in any way. Instead, the present disclosure is directed toward all novel and nonobvious features and aspects of the various disclosed methods, apparatus, and equivalents thereof, alone and in various combinations and subcombinations with one another. The disclosed technology is not limited to any specific aspect or feature, or combination thereof, nor do the disclosed methods and apparatus require that any one or more specific advantages be present or problems be solved.

As used in this application and in the claims, the singular forms "a," "an" and "the" include the plural forms unless the context clearly dictates otherwise. Additionally, the term "includes" means "comprises." The phrase "and/or" can mean "and," "or," "both," or "two or more of."

Although the operations of some of the disclosed methods and apparatus are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods and apparatus can be used in conjunction with other methods and apparatus. Additionally, the description sometimes uses terms like "determine" and "select" to describe the disclosed methods. These terms are high-level abstractions of the actual operations that are performed. The actual operations that correspond to these terms will vary depending on the particular implementation and are readily discernible by one of ordinary skill in the art. The disclosed embodiments can be implemented in, for example, a wide variety of integrated circuits, computer systems, and/or software configurations.

Any of the methods described herein can be performed or simulated (at least in part) using software comprising computer-executable instructions stored on one or more computer-readable media (e.g., communication media, storage media, tangible media, or the like). Furthermore, any intermediate or final results of the disclosed methods can be stored on one or more computer-readable media. Any such software can be executed on a single computer, on a networked computer (for example, via the Internet, a wide-area network, a local-area network, a client-server network, or other such network), a set of computers, a grid, or the like. For clarity, only certain selected aspects of the software-based implementations are described. At least some other details that are well known in the art are omitted. For the same reason, computer hardware is not described in further detail. Items referred to herein as "components" can be implemented as software and/or hardware components. It should be understood that the disclosed technology is not limited to any specific computer language, program, or computer. For instance, a wide variety of commercially available computer languages, programs, and computers can be used.

FIG. 1 shows a block diagram of an exemplary embodiment of a system 100 that can be used for managing clinical medical error information, particularly clinical medical error information that is described using two or more heterogeneous taxonomies. The system 100 comprises an interoperability component 110 that handles information provided by, for example, one or more users 142, 144, 146 and one or more descriptions of clinical medical error taxonomies 160, 162, 164. The one or more descriptions of the clinical error taxonomies can be stored, for example, in one or more databases. The interoperability component 110 comprises a classification component 120 and a translation component 130. Further embodiments of the interoperability component 110 comprise a user interface (UI) component 140 for receiving information from and/or presenting information to the users 142, 144, 146. In additional embodiments, a rules component 150 provides rules (sometimes called "business rules") for managing data in the classification component 120 and/or the translation component 130. An administration component 170 can allow for management of the system 100, for example, by managing various aspects of the other components by approving or rejecting changes to data stored in the system. A search component 180 can provide search results for data related to the taxonomies 160, 162, 164. At least some of these components are described in more detail below.

Figure 2:
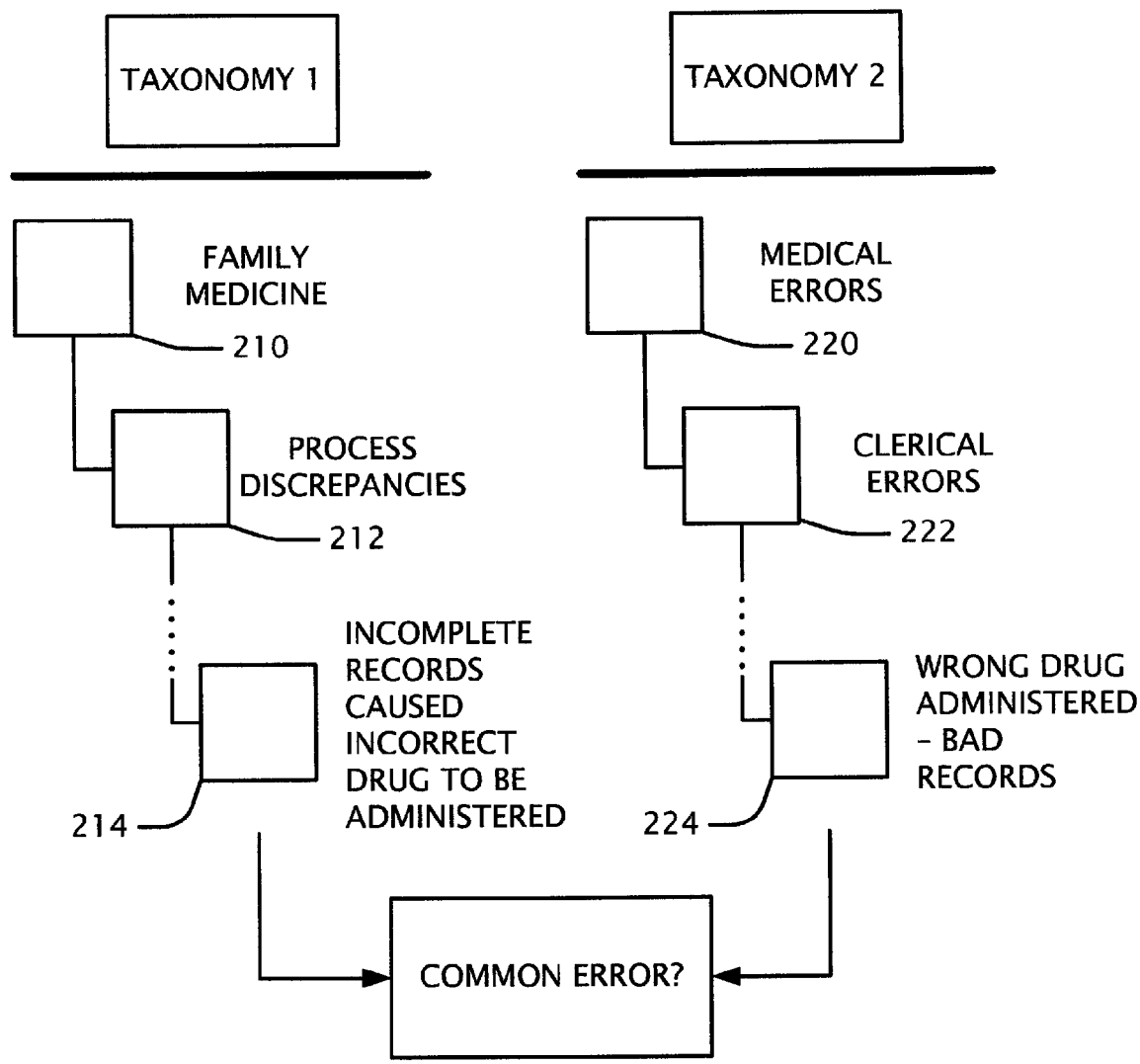
FIG. 2 shows a block diagram depicting two example heterogeneous clinical medical error taxonomies.

FIG. 2 shows a block diagram depicting two example heterogeneous clinical medical error taxonomies, Taxonomy 1 and Taxonomy 2. Taxonomy 1 categorizes clinical errors using multiple levels of categorization, for example categories 210, 212. The most specific level of clinical error category in this case is category 214, titled "Incomplete Records Caused Incorrect Drug to Be Administered." Taxonomy 2 also categorizes clinical errors using multiple levels of categorization (e.g., categories 220, 222), with a most specific category 224 titled in this example "Wrong Drug Administered—Bad Records." (For clarity, additional categories in the example taxonomies of FIG. 2 are not shown in this figure.) For the present example, it is assumed that categories 214 and 224 apply to overlapping subject matter. That is, at least some clinical medical errors placed in category 214 under Taxonomy 1 would most likely be placed in category 224 under Taxonomy 2. Without further information about Taxonomies 1 and 2, it is not apparent that such an overlap exists, particularly if a user handling clinical error information is familiar with only one of the two taxonomies. However, as described in more detail below, multiple taxonomies can be aggregated and organized using one or more taxonomies having unique identifiers for one or more categories.

Figure 3A:
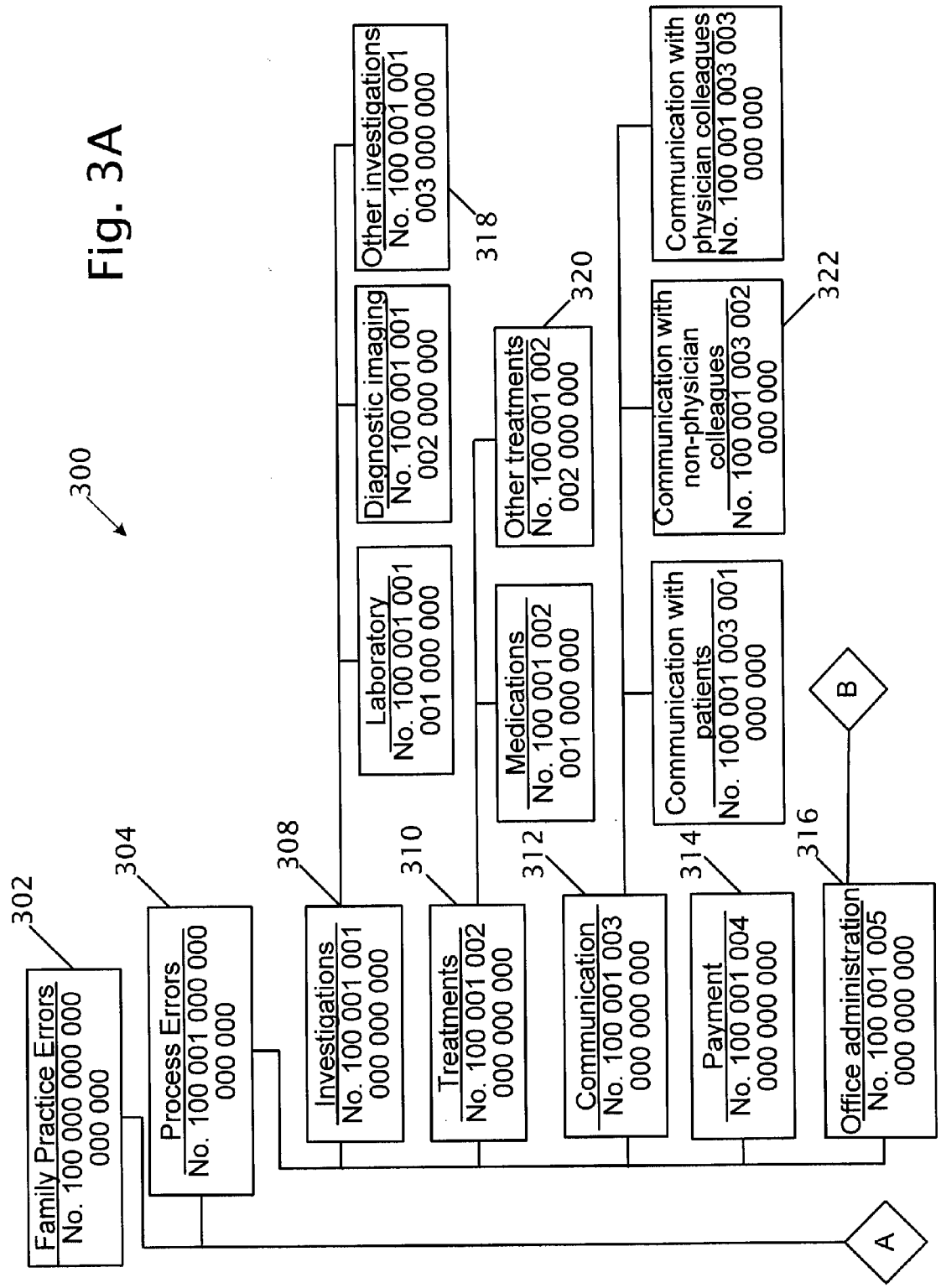
FIGS. 3A and 3B (which together comprise FIG. 3) show a block diagram of an exemplary clinical medical error taxonomy.
Figure 3B:
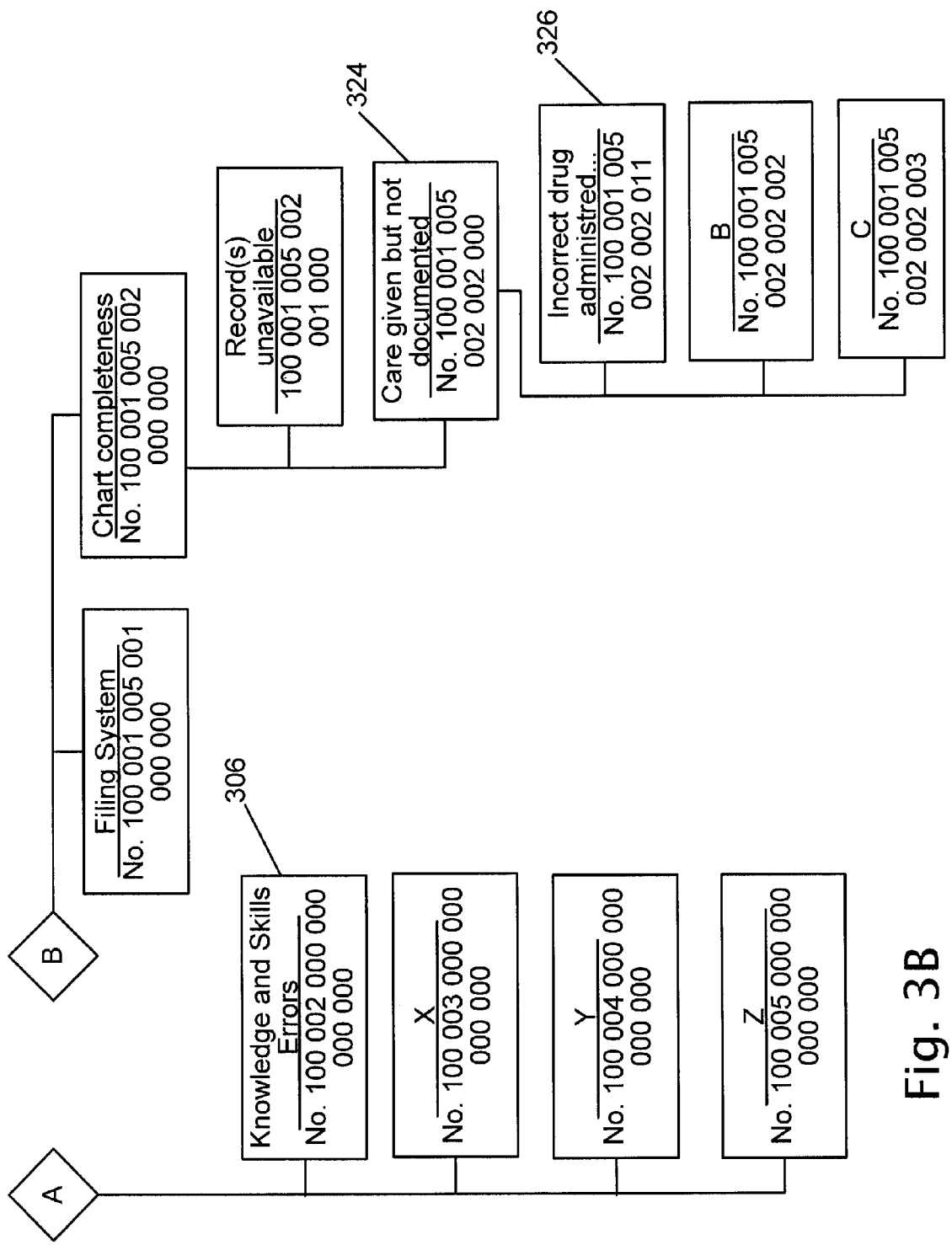

FIG. 3 shows a block diagram of an exemplary clinical error taxonomy 300. A box 302 represents a top level of the taxonomy 300 and indicates that this taxonomy generally pertains to errors in the area of "Family Practice." Additional taxonomies can cover a number of other areas in medical fields, for example, "Gynecology," "Pediatrics," and "Obstetrics." The box 302 is related to a subset of boxes, including boxes 304, 306, that represent sub-categories of errors within the area of "Family Practice." These are sometimes referred to herein as "nodes" of the taxonomy. In the depicted embodiment, these nodes include different groups of errors, for example, "Process Errors" (box 304) and "Knowledge and Skills Errors" (box 306). A given node can be related to a subset of nodes. For example, FIG. 3 shows that errors in the node "Process Errors" category can be divided among errors groups "Investigations," "Treatments," "Communication," "Payment" and "Office Administration." These error groups are nodes represented by boxes 308, 310, 312, 314, 316, respectively. As shown in FIG. 3, additional nodes can be used to more particularly categorize a given clinical error. (See, for example, boxes 318, 320, 322, 324.) In some embodiments, a lowest level of the taxonomy (represented, for example, by box 326) is comprised of categories of clinical errors known as "elements."

Figure 4A:
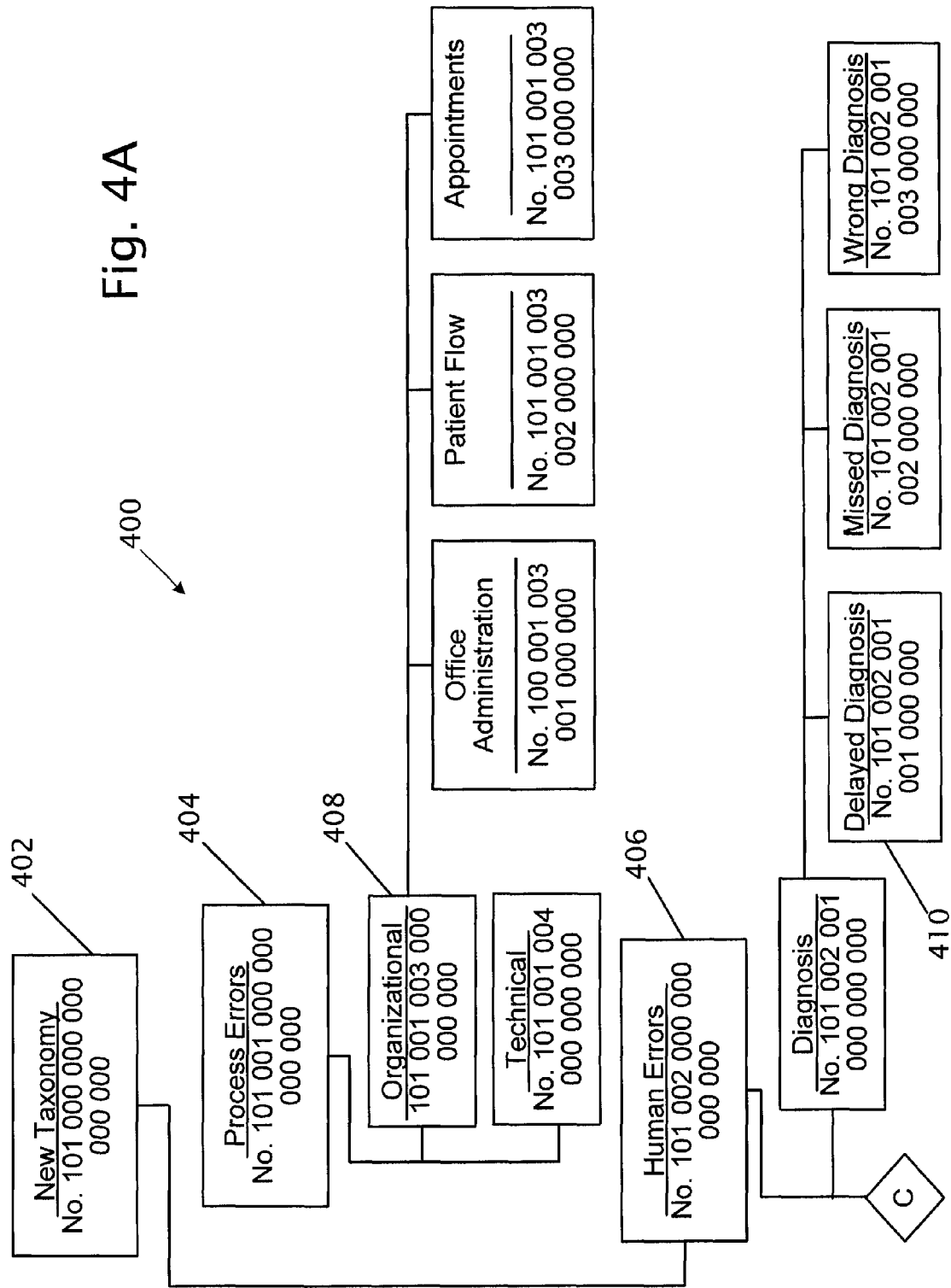
FIGS. 4A and 4B (which together comprise FIG. 4) show a block diagram of an exemplary clinical medical error taxonomy.
Figure 4B:
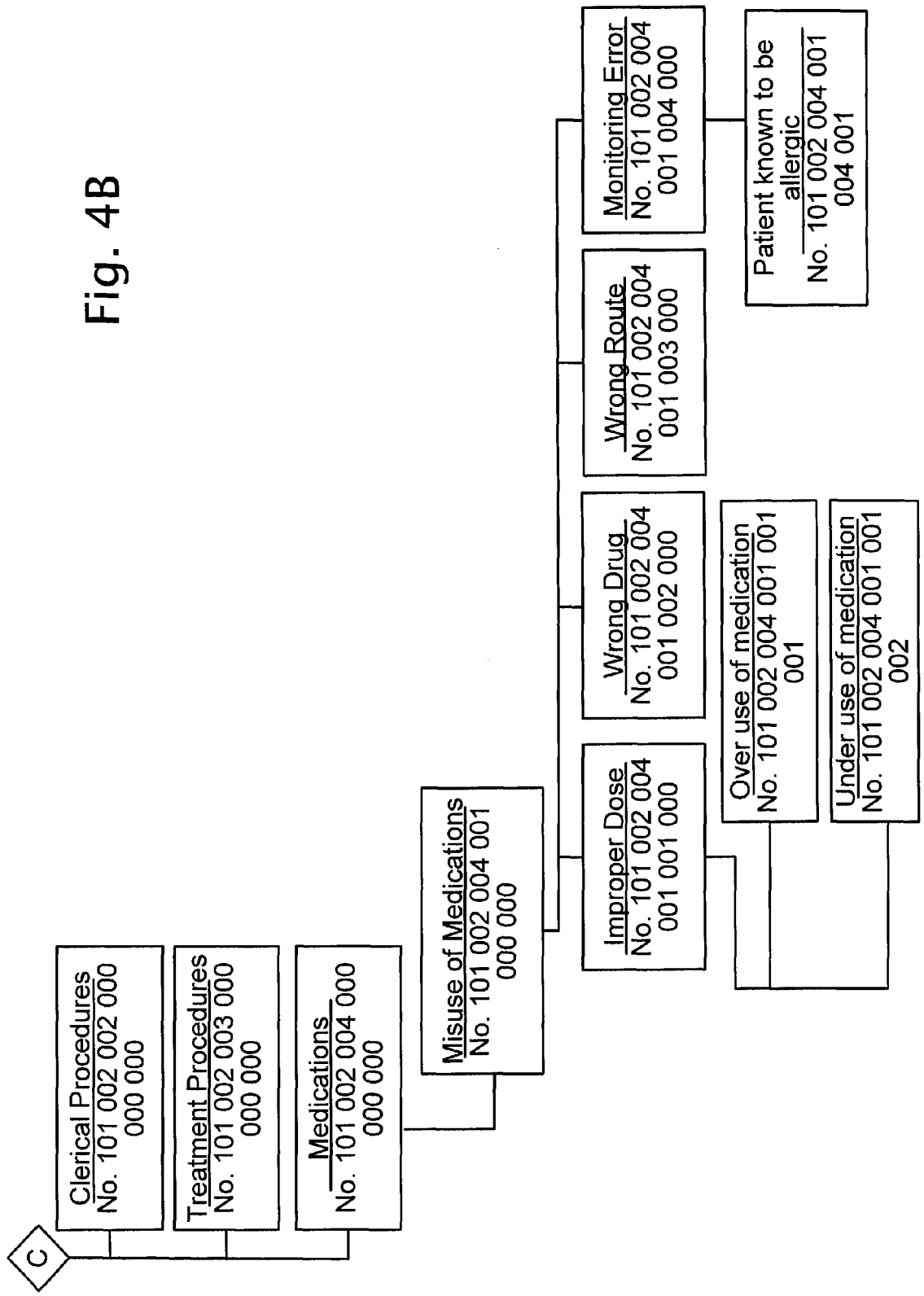

As another example, FIG. 4 shows a block diagram of an exemplary clinical error taxonomy 400. A top level of the taxonomy is represented by a box 402, and additional boxes (e.g., 404, 406, 408, 410) represent various categories of clinical errors. As used in this application, "master clinical error taxonomy," "master error taxonomy" and "master taxonomy" refer to taxonomies such as those in FIGS. 3 and 4 to which one or more other taxonomies are mapped, as explained below. The terms "original clinical error taxonomy," "original error taxonomy" and "original taxonomy" refer to taxonomies (such as such as Taxonomies 1 and 2 in FIG. 2) that are mapped to one or more master clinical error taxonomies.

The master clinical error taxonomies 300, 400 employ unique identifiers that are associated with nodes and/or elements. The identifier is unique in that, generally speaking, it is associated with exactly one node in exactly one master taxonomy description. In various embodiments the unique identifier has different formats and comprises, for example, letters and/or numbers. FIG. 5 shows a table 500 depicting an exemplary embodiment of one format for a unique identifier. A row 502 includes 18 digits that comprise the unique identifier. For convenience in presentation, in a row 504 these digits are labeled D1 through D18. In the depicted embodiment, the 18 digits are subdivided into six blocks (510, 512, 514, 516, 518, 520) of three digits each. One block (block 510) identifies the master taxonomy with which the unique identifier is associated, and some or all of the remaining blocks identify nodes at various levels in the master taxonomy. In the embodiment of FIG. 5, the blocks from left to right identify nodes in the associated master taxonomy with increasing depth (i.e., the block 510 identifies the master taxonomy, the block 512 identifies a node at the next highest level in the master taxonomy, and block 520 identifies a node or element at the lowest level in the master taxonomy.

The master clinical error taxonomies in FIGS. 3 and 4 employ this format for unique identifiers, with the box for each node or element containing an 18-digit number. For example, the box 302 of FIG. 3 bears the identifier "100 000 000 000 000 000," the box 304 has the identifier "100 001 000 000 000 000," and the box 308 has the identifier "100 001 001 000 000 000."

In further embodiments, the blocks 510, 512, 514, 516, 518, 520 are made up of differing numbers of digits. In additional embodiments, the format of the unique identifier can vary according to the particular taxonomy the identifier is associated with. For example, if the identifier is associated with a Master Taxonomy A, the identifier is interpreted as comprising one three-digit block and three five-digit blocks. However, if the identifier is associated with a Master Taxonomy B, the identifier is interpreted as comprising one three-digit block, one five-digit block, three three-digit blocks, and a one-digit block.

Figure 6:
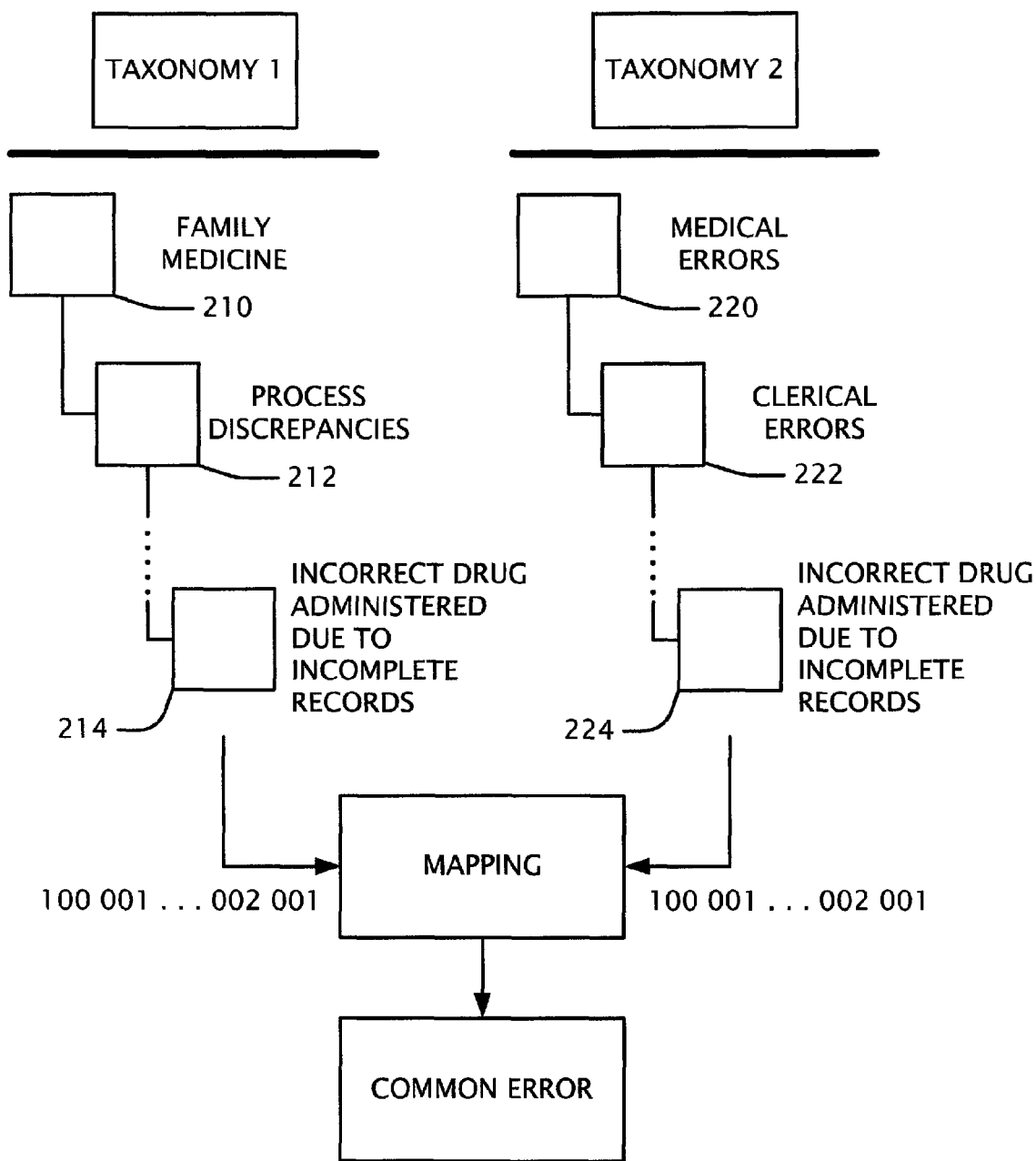
FIG. 6 shows the exemplary clinical error taxonomy of FIG. 3 applied to the taxonomies of FIG. 2.

FIG. 6 shows the exemplary clinical error taxonomy 300 of FIG. 3 applied to Taxonomy 1 and Taxonomy 2 of FIG. 2. In FIG. 6, categories 214 and 224 of Taxonomies A, B respectively, are labeled as both corresponding to element 326 of the taxonomy 300, "Incorrect Drug Administered Due to Incomplete Records." The categories 214, 224 are both associated with the 18-digit unique identifier for this element ("100 001 005 002 002 001"). Accordingly, when these associations are provided to a mapping component, the errors classified in category 214 by Taxonomy 1 and in category 224 by Taxonomy 2 can be identified as being errors of a common type. This information can be useful, for example, when searching a database of clinical errors described by Taxonomies 1 and 2.

Figure 7:
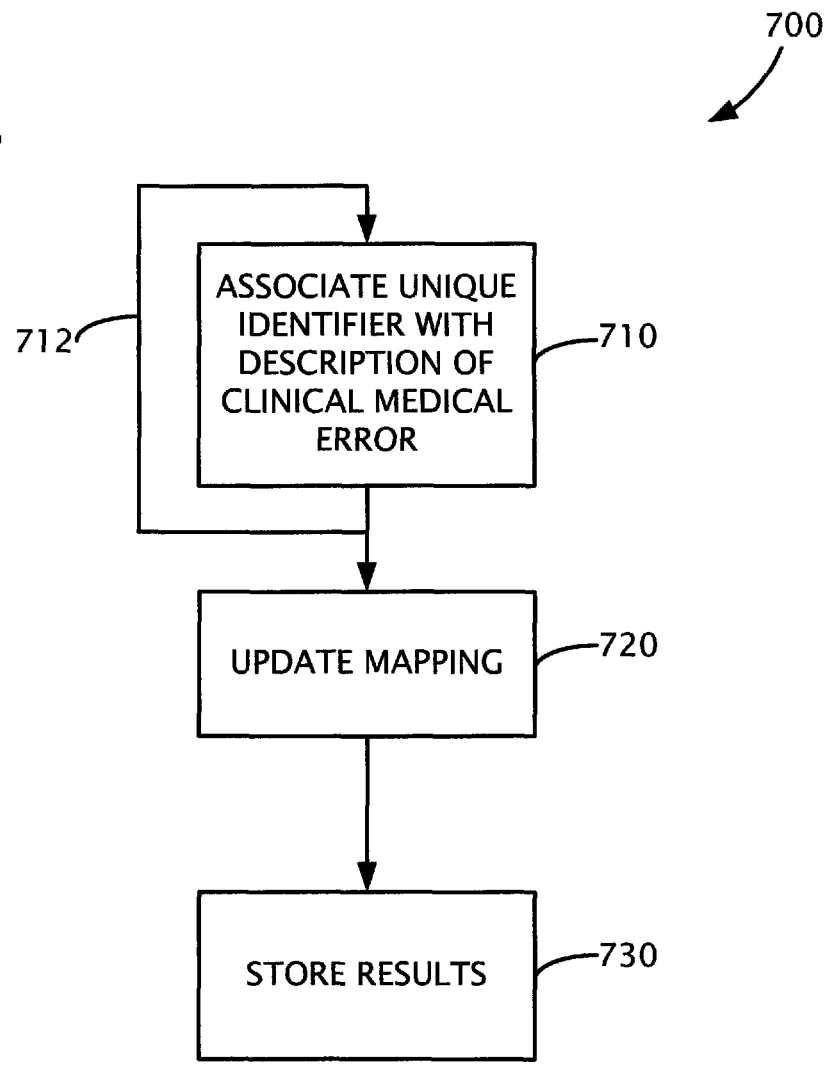
FIG. 7 shows a block diagram of an exemplary embodiment of a method of managing a plurality of clinical error taxonomies.

FIG. 7 shows a block diagram of an exemplary embodiment of a method 700 of managing a plurality of clinical error taxonomies using a system such as the system 100. The method 700 can allow a user to modify association of one or more original taxonomies with one or more master taxonomies by, for example, adding, deleting, or changing an association. In a method act 710, a description of a clinical medical error category (e.g., a node and/or element) in an original taxonomy is associated with a node or element in a master clinical error taxonomy. Generally, this association is made based at least in part on information provided by one or more users, such as the users 142, 144, 146, who are at least somewhat familiar with the taxonomy in which the clinical error is originally described (e.g., one of the taxonomies 160, 162, 164 of FIG. 1). For example, in some embodiments the user can examine a description of a master taxonomy (e.g., a chart such as those shown in FIGS. 3 and 4) and select the node or element in the master taxonomy that seems to best correspond to a particular category in the original taxonomy. The selection can be made, for example, using one or more menus or software wizards, or by providing a unique identifier. In some embodiments, the method act 710 is repeated for one or more nodes and/or elements in the original taxonomy (as indicated by an arrow 712), for example, until most or all nodes and/or elements in the original taxonomy are associated with a unique identifier in the master taxonomy. In particular embodiments, more than one node and/or element in the original taxonomy can be associated with a particular unique identifier in the master taxonomy. In at least some embodiments it is not necessary for a node and/or element in the original taxonomy to be associated with a unique identifier for a node and/or element at the same level in the master taxonomy. For example, a mid-level node in the original taxonomy can be associated with a unique number for an element in the master taxonomy.

The method act 710 is performed by the classification component 120 of system 100 based on, for example, inputs received by the UI component 140 from one or more users 142, 144, 146. In a method act 720, the associations created during the method act 710 are provided to the translation component 130. The translation component 130 maintains a mapping of the unique identifiers associated with various nodes and/or elements of the taxonomies 160, 162, 164, and the method act 720 allows the mapping to be updated. The mapping can be stored in one or more computer-readable media, for example as a list or a database. The mapping can be used in conjunction with, for example, searches executed using the search component 180. In method act 730, results related to the method acts 710, 720 can be stored in one or more computer-readable media. In some embodiments, the updating of the method act 720 can occur at predetermined intervals (e.g., 1-hour intervals, 24-hour intervals, and/or intervals of other lengths).

Figure 8:
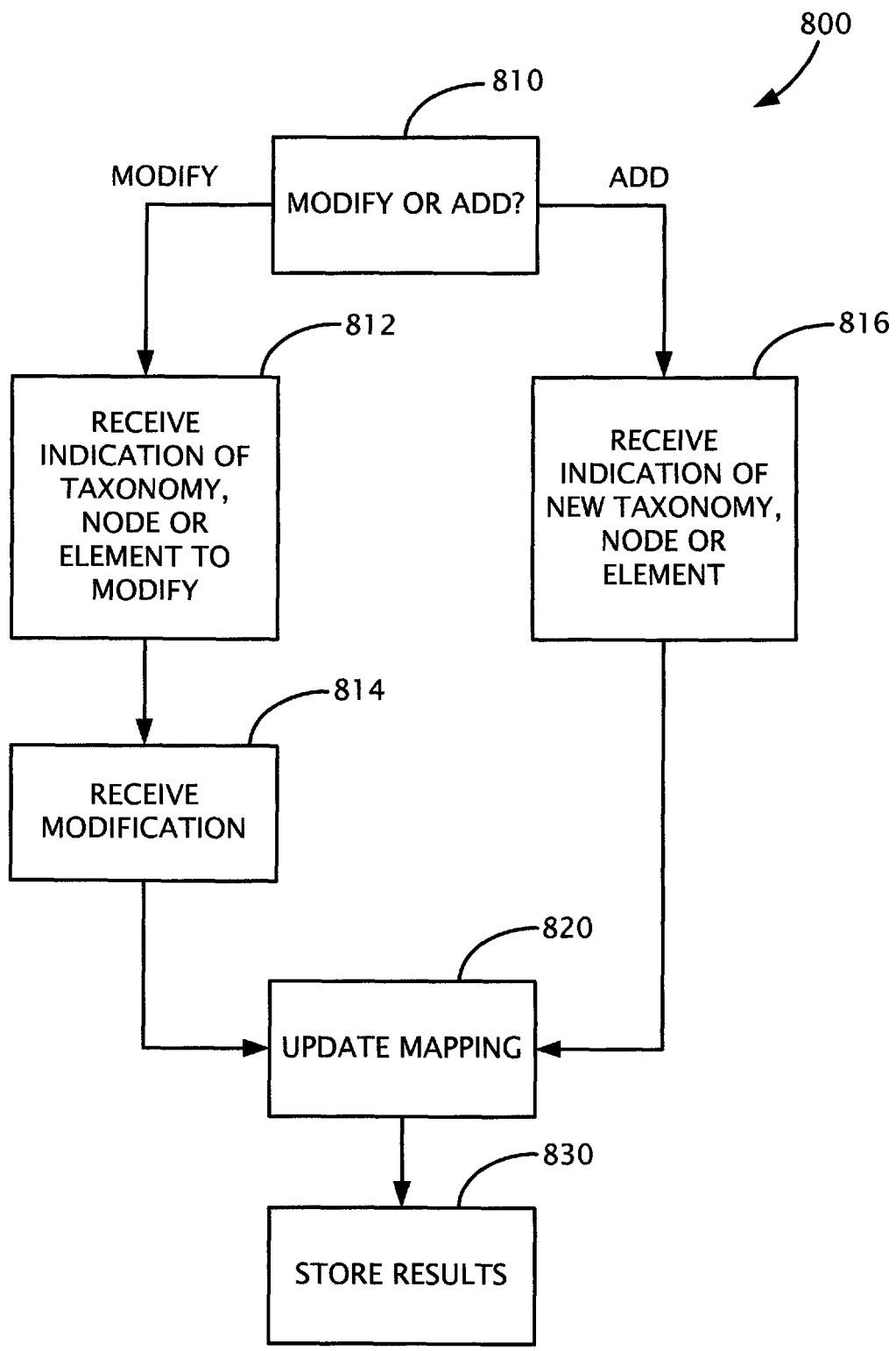
FIG. 8 shows a block diagram of an exemplary embodiment of a method for modifying and/or adding one or more master taxonomies.

In some embodiments, a user can modify and/or add one or more master taxonomies, for example, according to the exemplary method 800 shown in FIG. 8. In a method act 810 the system receives an indication of whether a user wishes to modify an existing master taxonomy, node or element or add a new master taxonomy, node or element. If the user wishes to make a modification, the system 100 receives from the user an indication of the taxonomy, node or element that is to be modified (method act 812), along with an indication of the modification (method act 814). In various embodiments, modifications can include, for example: changing the name(s) of one or more master taxonomies, nodes and/or elements; changing the unique identifier(s) associated with one or more master taxonomies, nodes and/or elements; and changing the relationships of one or more nodes and/or elements with respect to one or more other nodes and/or elements in the master taxonomy. Once the modification is complete, the mapping in the translation component 130 is updated (method act 820), and the results of the modification are stored in one or more computer-readable media (method act 830).

If the user wishes to make an addition, the system 100 receives an indication of the new master taxonomy, node and/or element in a method act 816. The indication can comprise, for example: names and/or unique identifiers for the new taxonomy, node and/or element, as well as descriptions of how the new element and/or node relates to pre-existing taxonomies, nodes and/or elements. Once the addition is complete, the mapping in the translation component 130 is updated (method act 820), and the results of the modification are stored in one or more computer-readable media (method act 830).

In further embodiments, a user can select one or more master taxonomies, nodes and/or elements for deletion. A command for a deletion can be accompanied with information regarding how one or more elements and/or nodes should be changed in light of the deletion. A successful deletion can be followed by updating the mapping in the translation component 130 and storing the results of the modification in one or more computer-readable media.

In particular embodiments the updating of the mapping in the method act 720 and/or method act 820 can be performed according to one or more rules in the rules component 150. One exemplary rule instructs the system 100 to proceed as follows: For a taxonomy, node and/or element that a user wishes to add to the system 100, the system 100 checks for the existence of the taxonomy, node and/or element in the mapping in translation component 130 using, for example, a unique identifier. If the taxonomy, node and/or element does not already exist, then it is added to the mapping. For a taxonomy, node and/or element that the user wishes to modify, the system 100 checks for the existence of the taxonomy, node and/or element in the mapping in translation component 130 using, for example, a unique identifier. If the taxonomy, node and/or element exists, then it is modified in the mapping. For taxonomy, node and/or element that the user wishes to delete, the system 100 locates the item using, for example, the unique identifier, and then deletes the item.

In another example, a rule in the rules component 150 is used to determine whether two clinical errors, described in different original taxonomies and each associated with a unique identifier, are classified in the same classification according to a master taxonomy. Generally, the rule causes the unique identifiers of the clinical errors to be compared. If the unique identifiers are the same, then the errors are in the same master taxonomy classification.

Generally, two or more unique identifiers are compared using one or more comparison techniques known in computer science. In particular embodiments, the digits of two or more 18-digit identifiers are compared left to right.

According to some embodiments, a rule in the rules component 150 can be implemented using one or more programming languages.

In further embodiments, users can make the changes described in FIGS. 7 and/or 8 only after providing authentication data (e.g., a user name and/or password) to the system 100. In at least some embodiments, one or more of the additions, modifications and/or deletions described in FIGS. 7 and/or 8 can be suspended subject to administrative approval. The administration component 170 can be used to approve or deny one or more changes to the associations between a master taxonomy and an original taxonomy or to a master taxonomy itself. The administration component 170 can also be used to manage user accounts, e.g., to add, suspend or remove a user account from the system 100, or to change user privileges or authentication data. The system 100 can be configured to notify a user of decisions made by the administrator regarding the user's actions with respect to the system 100.

Additional embodiments of the system 100 can provide results for search queries, using the search component 180, for example. In some embodiments, a query string (containing, e.g., a unique identifier) is provided to the system from a user, and the system 100 returns results comprising, e.g., clinical errors from one or more original taxonomies that are in categories associated with the unique identifier.

Figure 9:
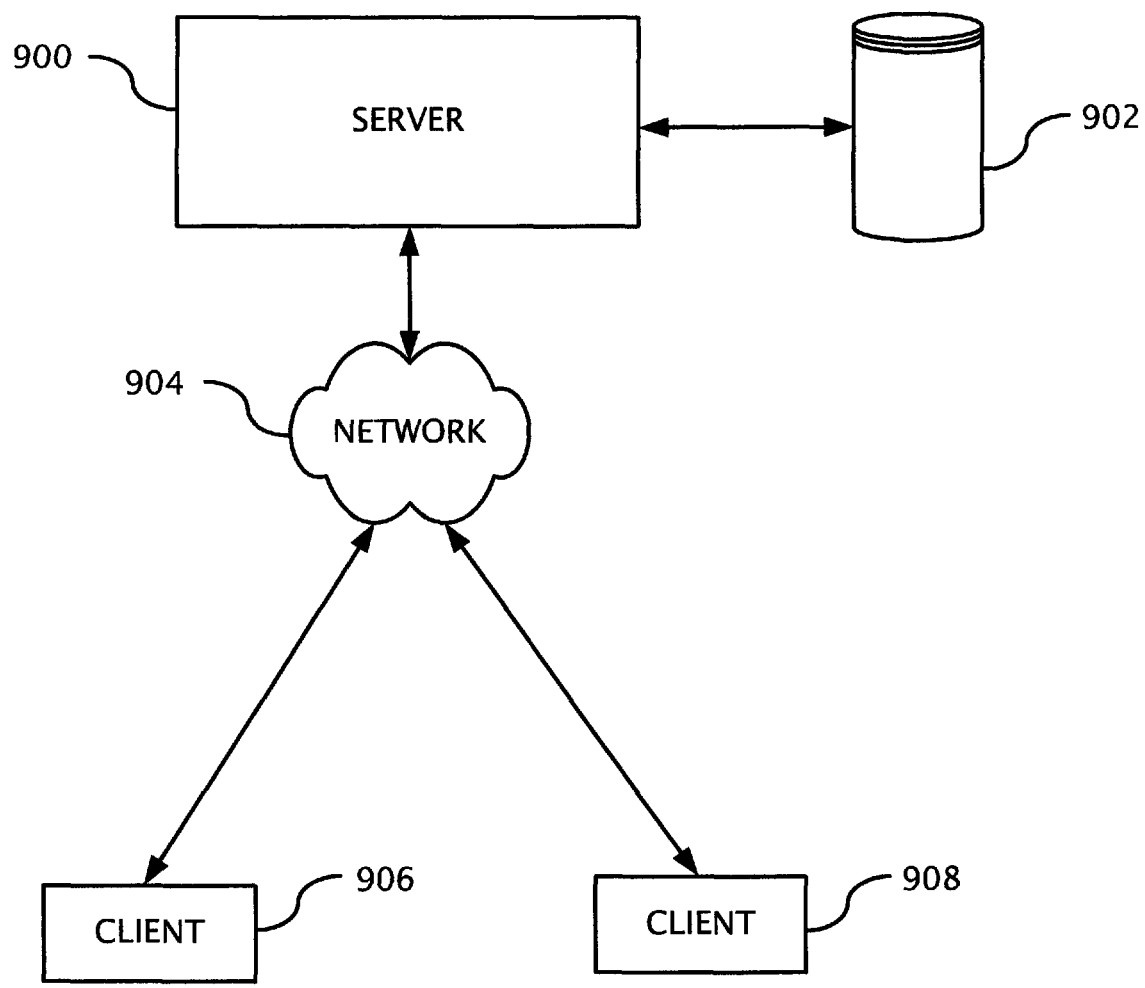
FIG. 9 is a schematic block diagram of a network suitable for performing any of the disclosed methods or to generate any of the disclosed screening results.

Any of the aspects of the technologies described above may be performed using a distributed computer network. FIG. 9 shows one suitable exemplary network. A server computer 900 can have an associated storage device 902 (internal or external to the server computer). For example, the server computer 900 can be configured to generate any of the disclosed interoperation method embodiments. The server computer 900 can be coupled to a network, shown generally at 904, which can comprise, for example, a wide-area network, a local-area network, a client-server network, the Internet, or other suitable network. One or more client computers, such as those shown at 906, 908, may be coupled to the network 904 using a network protocol. The work may also be performed on a single, dedicated workstation, which has its own memory and one or more CPUs. Any of the operations described herein as involving user input can be performed using technologies wherein multiple users edit a collective body of data. For example, a first user may be able to review and change information provided to the system 100 by a second user. Such scenarios are sometimes referred to names like "wiki" or "peer-to-peer."

Figure 10:
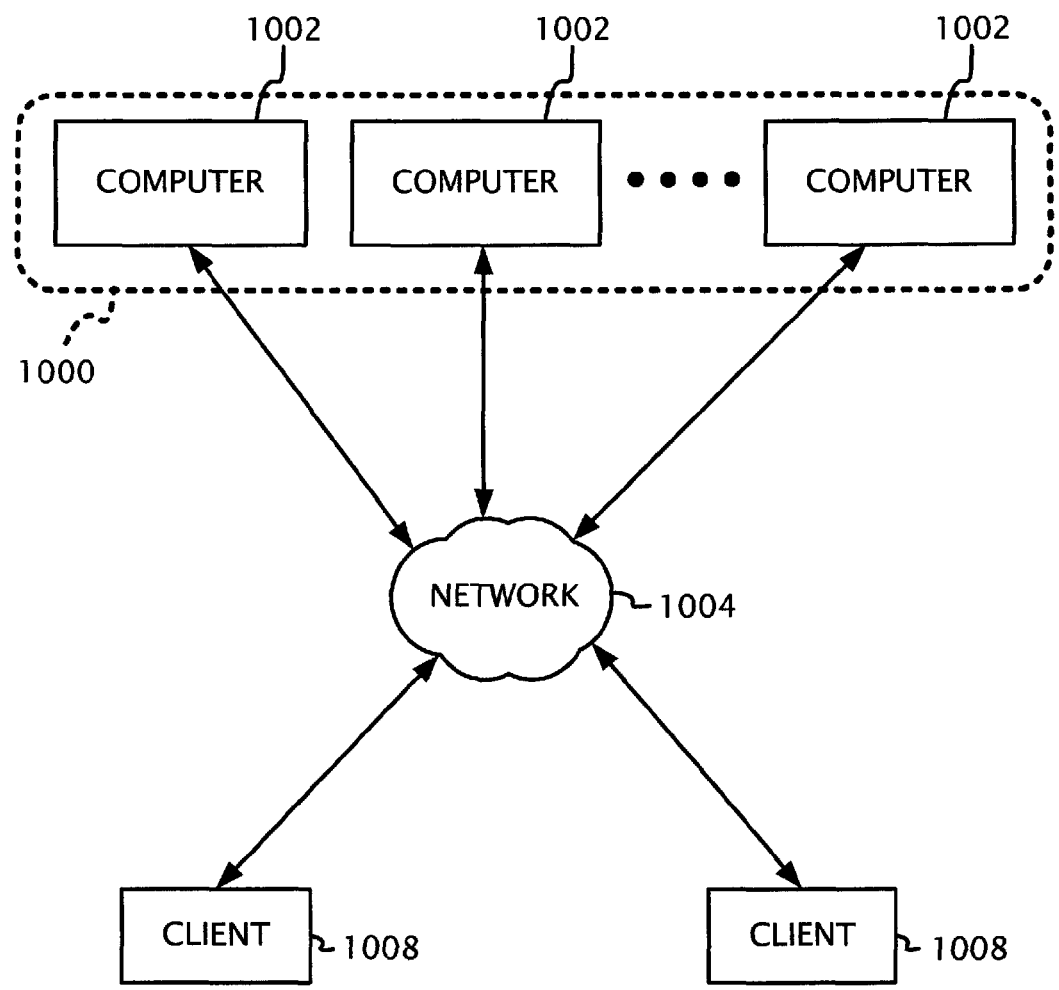
FIG. 10 is a schematic block diagram of a distributed computing network suitable for performing any of the disclosed methods.

FIG. 10 shows another exemplary network. One or more computers 1002 communicate via a network 1004 and form a computing environment 1000 (for example, a distributed computing environment). Each of the computers 1002 in the computing environment 1000 can be used to perform at least a portion of the screening process. The network 1004 in the illustrated embodiment is also coupled to one or more client computers 1008.

Figure 11:
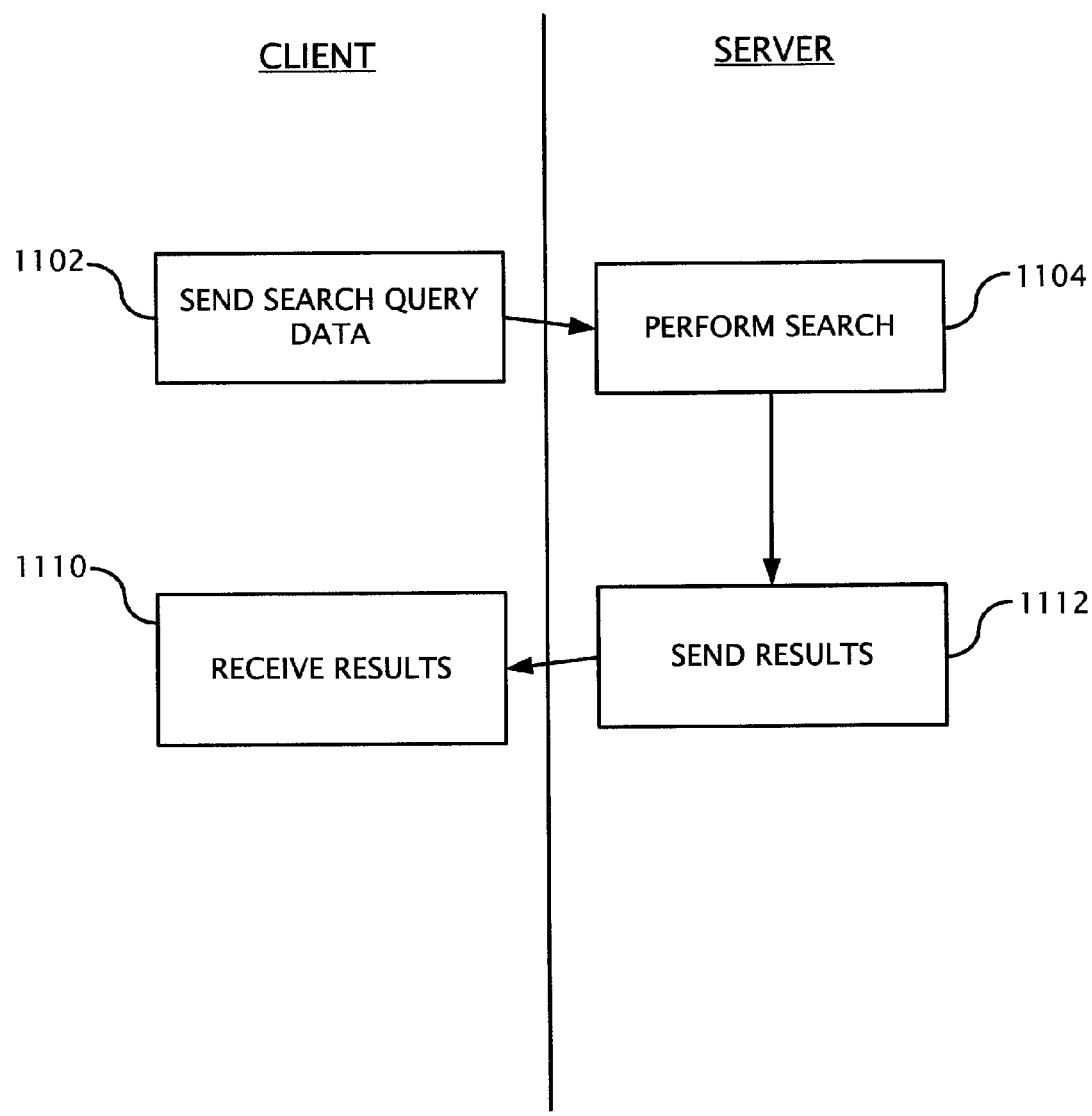
FIG. 11 is a flowchart illustrating how an embodiment of disclosed search results can be generated in the network of FIG. 9 and FIG. 10.

FIG. 11 shows that clinical medical error searches can be performed using a remote server computer (such as the server computer 900 shown in FIG. 9) or a remote computing environment (such as the computing environment 1000 shown in FIG. 10) in order to generate search results classified using the disclosed technology. At a method act 1102, for example, the client computer sends a search query to the remote server or computing environment. In a method act 1104, the search is performed by the remote server or by respective components of the remote computing environment. At a method act 1112, the remote server or computing environment sends the search results to the client computer, which receives the results at a method act 1110.

In some embodiments, at least some of the technologies described above can be implemented using components that combine one or more aspects of a thin client, a thick client, and a web service. A client computer can be updated when the client computer is synchronized with a server, for example.

In view of the many possible embodiments to which the principles of the disclosed technologies may be applied, it should be recognized that the illustrated embodiments are only examples of the technologies and should not be taken as limiting the scope of the invention. Rather, the scope of the invention is defined by the following claims. We therefore claim as our invention all that comes within the scope and spirit of these claims.

We claim:

1. A computer system comprising computer-executable instructions stored on one or more computer-readable storage media, the instructions comprising:
    a first software component configured to receive user-provided descriptions for at least a first original taxonomy and a second original taxonomy for classifying clinical medical errors, the at least first and second original taxonomies comprising heterogeneous clinical medical error categories;
    a second software component configured to generate associations of unique identifiers with the categories of the first original taxonomy and the categories of the second original taxonomy, the unique identifiers corresponding to standardized categories of a master clinical medical error taxonomy, the original taxonomies being created independently of the master taxonomy, the unique identifiers being alpha-numeric codes subdivided into a plurality of blocks of one or more characters, the blocks representing nodes at different levels of categorization within the master taxonomy;
    a third software component configured to generate a mapping of the first and second original taxonomies to one another, the mapping comprising correlating categories of the first original taxonomy with categories of the second original taxonomy that are associated with common unique identifiers;
    a fourth software component configured to receive user-provided changes to relationships between one or more of the nodes of the master taxonomy with respect to one or more other of the nodes of the master taxonomy;
    a fifth software component configured to modify the unique identifiers of the master taxonomy in response to the received user-provided changes to the relationships between the nodes of the master taxonomy;
    a sixth software component configured to, in response to modifications of the unique identifiers, receive user-provided modifications to the associations of the unique identifiers of the master taxonomy with the categories of the first original taxonomy and the categories of the second original taxonomy; and
    a seventh software component configured to update the mapping of the first and second original taxonomies to one another based on the received user-provided modifications of the sixth software component.

2. The system of claim 1, wherein modifying the unique identifiers of the master taxonomy comprises changing the characters of the blocks that represent the nodes.

3. The system of claim 1, wherein the leftmost block identifies the master taxonomy, the next block to the right identifies a node at a highest level in the master taxonomy, and the rightmost block identifies a node at a lowest level in the master taxonomy.

4. The system of claim 1, further comprising a set of one or more rules for managing data in the second and third software components.

5. The system of claim 1, wherein at least one of the first software component, the second software component and the third software component is configured to be executed on a first computer, and wherein at least one of the first software component, the second software component and the third software component is configured to be executed on a second computer.

6. The system of claim 1, further comprising a search software component configured to search clinical medical error data based on the mapping of the first and second original taxonomies to one another.

7. The system of claim 1, further comprising an administrative software component configured to regulate user-provided modifications from a plurality of non-administrator users.

8. The system of claim 7, wherein the administrative software component is configured to approve or deny the user-provided modifications based on authentication data received from users.

9. The system of claim 1, wherein the mapping of the original taxonomies to one another identifies one or more clinical medical error types common to the original taxonomies.

10. One or more computer-readable media comprising instructions that cause a computer to perform a method comprising:
    receiving a description of a first clinical medical error category in a first clinical medical error taxonomy;
    receiving a description of a second clinical medical error category in a second clinical medical error taxonomy, the first and second taxonomies having heterogeneous taxonomic structures;
    creating a first association of the description of the first clinical medical error category with a unique identifier of a master clinical medical error category in a master clinical medical error taxonomy, the unique identifier being a numeric code subdivided into a plurality of blocks, each block representing a node at a different level of categorization within the master taxonomy, the first association being based on a similarity of subject matter encompassed by the first category and the master category, the first and second taxonomies being created independently of the master taxonomy;

creating a second association of the description of the second clinical medical error category with the unique identifier, the second association being based on a similarity of subject matter encompassed by the second category and the master category;

creating a third association of the first clinical medical error category and the second clinical medical error category based on the first and second associations;

storing an indication of the third association in one or more computer-readable media;

receiving a user-provided modification to the relationships between one or more of the nodes of the master taxonomy with respect to one or more other of the nodes of the master taxonomy;

modifying the unique identifier based on the modification to the relationships between the nodes of the master taxonomy;

receiving one or more user-provided modifications to the first and second associations based on the modifications to the unique identifier; and updating the third association based on the received modifications to the first and second associations.

11. The one or more computer-readable media of claim 10, wherein the description of the first clinical medical error category in the first clinical medical error taxonomy is received over a network.

12. The one or more computer-readable media of claim 10, wherein the method further comprises automatically updating the third association at predetermined time intervals to incorporate user-provided modifications to the first and second associations received during the intervals.

13. The one or more computer-readable media of claim 10, wherein the user-provided modifications are received from one or more non-administrator users and the method further comprises updating the first and second associations based on the user-provided modifications after the user-provided modifications are approved by an administrator.

14. The one or more computer-readable media of claim 13, wherein the user-provided modifications are received from a plurality of non-administrator users.

15. The one or more computer-readable media of claim 10, wherein the method further comprises:
storing an indication of the first and second associations in one or more computer-readable media.

16. The one or more computer-readable media of claim 10, the method further comprising:
making a determination, based at least in part on the unique identifier, of whether a clinical medical error associated with the first clinical medical error category is considered to be similar to a clinical medical error associated with the second clinical medical error category; and
storing the determination in one or more computer-readable media.

17. One or more computer-readable media comprising instructions that cause one or more computers to perform a method comprising:
identifying one or more unique identifiers associated with respective master categories of a master taxonomy for classifying information in a field, the unique identifiers comprising a plurality of blocks of alpha-numeric characters, each block corresponding to a node at a different categorization level within the master taxonomy, the blocks from left to right identifying nodes in the master taxonomy with increasing depth;

receiving at least a first original taxonomy and a second original taxonomy for classifying information in the field, the original taxonomies being created independently of the master taxonomy and having original categories that are distinct from the master categories, the original categories of the first original taxonomy being distinct from the original categories of the second original taxonomy;

identifying one or more portions of the first original taxonomy that encompass subject matter similar to respective portions of the master taxonomy and identifying one or more portions of the second original taxonomy that encompass subject matter similar to the respective portions of the master taxonomy, the identified portions of the first and second original taxonomies comprising one or more original categories and the respective portions of the master taxonomy comprising one or more master categories;

associating the original categories that comprise the identified portions of the original taxonomies with the one or more unique identifiers associated with respective master categories that comprise the respective portions of the master taxonomy;

associating the original categories that comprise the identified portions of the first original taxonomy with the original categories that comprise the identified portions of the second original taxonomy;

receiving from a plurality of non-administrator users user-provided changes to relationships between one or more of the nodes of the master taxonomy with respect to one or more other of the nodes;

modifying the unique identifiers in response to the user-provided changes to the relationships between the nodes; and receiving from a plurality of non-administrator users user-provided modifications to the associations of the original categories with the modified unique identifiers, and in response, updating the associations of the categories of the first taxonomy with the categories of the second taxonomy.

18. The one or more computer-readable media of claim 17, wherein the method further comprises:
receiving authenticating data from the users;
receiving instructions from the users to modify one or more associations between the unique identifiers and the master categories;
modifying the associations between the unique identifiers and the master categories according to the instructions;
updating the associations between the unique identifiers and the original categories based on the modifications to the associations between the unique identifiers and the master categories; and
updating the associations between the original categories of the first original taxonomy and the original categories of the second original taxonomy based on the modifications to the associations between the unique identifiers and the master categories.

* * * * *